United States Patent [19]

Hoegerle et al.

[11] 4,391,810
[45] Jul. 5, 1983

[54] 2-METHYL-4-N,N-DIMETHYLCARBAMOYLOXY-6-AMINO-PYRIMIDINES AND SALTS THEREOF, PROCESSES FOR PRODUCING THEM, AND THEIR USE FOR COMBATING PESTS

[75] Inventors: Karl Hoegerle; Laurenz Gsell, both of Basel; Rudolf Wehrli, Rheinfelden, all of Switzerland

[73] Assignee: Ciba-Geigy Corporation, Ardsley, N.Y.

[21] Appl. No.: 335,936

[22] Filed: Dec. 30, 1981

[30] Foreign Application Priority Data

Jan. 6, 1981 [CH] Switzerland ............................. 31/81
Oct. 14, 1981 [CH] Switzerland ....................... 6571/81

[51] Int. Cl.³ .................... C07D 239/47; A01N 9/22
[52] U.S. Cl. .................................... 424/251; 544/319
[58] Field of Search ....................... 544/319; 424/251

[56] References Cited

U.S. PATENT DOCUMENTS 2,694,712 11/1954 Gysin ................................... 544/319
4,215,122 7/1980 Drabek ................................ 424/251

OTHER PUBLICATIONS

Pilinskaya, Tsitol. Genet, 14(6) 41–7 1980 (Abstract).

Primary Examiner—Robert Gerstl
Attorney, Agent, or Firm—Frederick H. Rabin

[57] ABSTRACT

2-Methyl-4-N,N-dimethylcarbamoyloxy-6-amino-pyrimidines, and salts thereof, of the formula

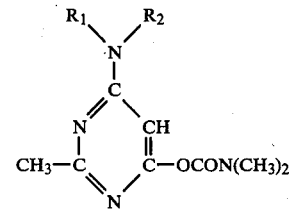

wherein $R_1$ and $R_2$ are each hydrogen, $C_1$–$C_5$-alkyl, $C_3$–$C_6$-cycloalkyl, $C_2$–$C_5$-alkenyl or $C_2$–$C_5$-alkynyl, or together they are a $C_2$–$C_5$-alkylene group; a process for producing these pyrimidines; and their use for combating pests.

9 Claims, No Drawings

2-METHYL-4-N,N-DIMETHYLCARBAMOYLOXY-6-AMINO-PYRIMIDINES AND SALTS THEREOF, PROCESSES FOR PRODUCING THEM, AND THEIR USE FOR COMBATING PESTS

The present invention relates to 2-methyl-4-N,N-dimethylcarbamoyloxy-6-aminopyrimidines and salts thereof, to processes for producing them, and to their use for combating pests.

The pyrimidines have the formula

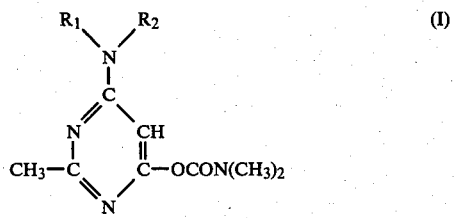

wherein $R_1$ and $R_2$ are each hydrogen, $C_1$-$C_5$-alkyl, $C_3$-$C_6$-cycloalkyl, $C_2$-$C_5$-alkenyl or $C_2$-$C_5$-alkynyl, or together they are a $C_2$-$C_5$-alkylene group.

Inorganic acids for forming salts are for example: HCl, $H_2SO_4$, HBr and $H_3PO_4$, and organic acids for this purpose are for example: saturated and unsaturated mono-, di- and tricarboxylic acids, such as formic acid, acetic acid, oxalic acid, phthalic acid, succinic acid and citric acid.

The alkyl, alkenyl or alkynyl groups denoted by $R_1$ and $R_2$ can be straight-chain or branched-chain. Examples of such groups are, inter alia: methyl, ethyl, propyl, isoproyl, n-, i-, sec- or tert-butyl, n-pentyl and isomers thereof, allyl, propenyl and propargyl. Examples of cycloalkyl groups in the case of $R_1$ and $R_2$ are: cyclopropyl, cyclopentyl and cyclohexyl, preferably cyclopropyl.

Compounds of the formula I which are preferred on account of their action are those wherein $R_1$ and $R_2$ are each hydrogen, $C_1$-$C_4$-alkyl, cyclopropyl, allyl or propargyl, or $R_1$ and $R_2$ together with the nitrogen atom to which they are bound form the pyrrolidine ring.

The compounds of the formula I are produced by methods known per se, for example as follows:

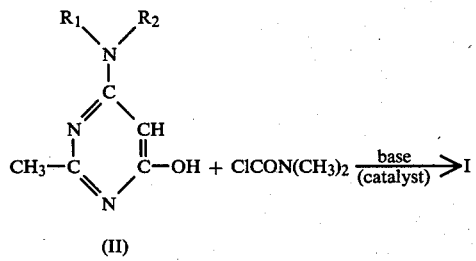

The symbols $R_1$ and $R_2$ in the formula II have the meanings defined under the formula I.

Suitable bases (catalysts) are in particular: tertiary amines, such as trialkylamines, dialkylanilines and p-dialkylaminopyridines. The reaction can also be performed however without a catalyst.

The process is carried out under normal pressure, at a temperature of $-25°$ to $150°$ C., preferably at $50°$ to $100°$ C., and optionally in a solvent or diluent.

Suitable solvents or diluents are for example: ethers and ethereal compounds, such as diethyl ether, diisopropyl ether, dioxane and tetrahydrofuran; aromatic hydrocarbons, such as benzene, toluene and xylenes; ketones, such as acetone, methyl ethyl ketone and cyclohexanones; nitriles, such as acetonitrile; esters such as ethyl acetate and butyl acetate; as well as dimethylformamide, dimethylsulfoxide, methyl cyanide and halogenated hydrocarbons.

The starting materials of the formula II are novel; they can be produced however by known processes (cp. Example 1).

The compounds of the formula I are suitable for combating pests on animals and plants. Furthermore, these compounds also have fungicidal and plant-growth-regulating properties.

The compounds of the formula I are suitable in particular for combating insects, for example of the orders: Lepidoptera, Coleoptera, Homoptera, Heteroptera, Diptera, Thysanoptera, Orthoptera, Anoplura, Siphonaptera, Mallophaga, Thysanura, Isoptera, Psocoptera and Hymenoptera; and for combating mites and ticks of the order Acarina.

Compounds of the formula I are especially suitable for combating insects that damage plants, particularly insects that damage plants by sucking, in crops of ornamental plants and productive plants, especially in cotton, vegetable, rice and fruit crops.

Active substances of the formula I exhibit also a very good action against eating and biting insects, and likewise against flies, for example *Musca domestica*, and against mosquito larvae.

The compounds of the formula I are used either in an unmodified form or preferably together with auxiliaries customarily employed in formulation practice, and are thus processed in a known manner for example into the form of emulsion concentrates, directly sprayable or dilutable solutions, diluted emulsions, wettable powders, soluble powders, dusts or granulates, and also encapsulations in for example polymeric substances. The application processes, such as spraying, atomising, dusting, scattering or pouring, and likewise the type of composition, are selected to suit the objects to be achieved and the given conditions.

The formulations, that is to say, the compositions or preparations containing the active substance of the formula I and optionally a solid or liquid additive, are produced in a known manner, for example by the intimate mixing and/or grinding of the active substances with extenders, such as with solvents, solid carriers and optionally surface-active compounds (tensides).

Suitable solvents are: aromatic hydrocarbons, preferably the fractions $C_8$ to $C_{12}$, such as xylene mixtures or substituted naphthalenes, phthalic esters, such as dibutyl- or dioctylphthalate, aliphatic hydrocarbons, such as cyclohexane or paraffins, alcohols and glycols, as well as ethers and esters thereof, such as ethanol, ethylene glycol, ethylene glycol monomethyl or -ethyl ethers, ketones such as cyclohexanone, strongly polar solvents, such as N-methyl-2-pyrrolidone, dimethylsulfoxide or dimethylformamide, as well as optionally epoxidised vegetable oils, such as epoxidised coconut oil or soybean oil; or water.

The solid carriers used, for example for dusts and dispersible powders, are as a rule natural mineral fillers, such as calcite, talcum, kaolin, montmorillonite or attapulgite. In order to improve the physical properties, it is also possible to add highly dispersed silicic acid or highly dispersed absorbent polymers. Suitable granulated adsorptive carriers are porous types, for example pumice, ground brick, sepiolite or bentonite; and suitable nonsorbent carriers are materials such as calcite or sand. There can also be used a great number of pre-granulated materials of inorganic or organic nature, such as in particular dolomite or ground plant residues.

Suitable surface-active compounds are, depending on the nature of the active substance of the formula I to be formulated, nonionic, cationic and/or anionic tensides having good emulsifying, dispersing and wetting properties. By 'tensides' are also meant mixtures of tensides.

Suitable anionic tensides are both so-called water-soluble soaps as well as water-soluble, synthetic, surface-active compounds.

Soaps which are applicable are the alkali metal, alkaline-earth metal or optionally substituted ammonium salts of higher fatty acids ($C_{10}$–$C_{22}$), for example the Na or K salts of oleic or stearic acid, or of natural fatty acid mixtures, which can be obtained for example from coconut oil or tallow oil. Also to be mentioned are the fatty acid-methyl-taurine salts.

So-called synthetic tensides are however more frequently used, particularly fatty sulfonates, fatty sulfates, sulfonated benzimidazole derivatives or alkylarylsulfonates. The fatty sulfonates or sulfates are as a rule in the form of alkali metal, alkaline-earth metal or optionally substituted ammonium salts, and contain an alkyl group having 8 to 22 C atoms, 'alkyl' including also the alkyl moiety of acyl groups, for example the Na or Ca salt of ligninsulfonic acid, of dodecylsulfuric acid ester or of a fatty alcohol sulfate mixture produced from natural fatty acids. Included among these are also the salts of sulfuric acid esters and sulfonic acids of fatty alcohol ethylene oxide adducts. The sulfonated benzimidazole derivatives preferably contain 2 sulfonic acid groups and a fatty acid group having 8–22 C atoms. Alkylarylsulfonates are for example the Na, Ca or triethanolamine salts of dodecylbenzenesulfonic acid, of dibutylnaphthalenesulfonic acid or of a naphthalenesulfonic acid-formaldehyde condensation product. Also suitable are corresponding phosphates, for example salts of the phosphoric ester of a p-nonylphenol-(4–14)-ethylene oxide adduct.

Suitable nonionic tensides are in particular polyglycol ether derivatives of aliphatic or cycloaliphatic alcohols, saturated or unsaturated fatty acids and alkylphenols, which can contain 3 to 30 glycol ether groups and 8 to 20 carbon atoms in the (aliphatic) hydrocarbon radical and 6 to 18 carbon atoms in the alkyl moiety of the alkylphenols.

Further suitable nonionic tensides are the water-soluble polyethylene oxide adducts, which contain 20 to 250 ethylene glycol ether groups and 10 to 100 propylene glycol ether groups, with polypropylene glycol, ethylenediaminopolypropylene glycol and alkylpolypropylene glycol having 1 to 10 carbon atoms in the alkyl chain. The compounds mentioned usually contain 1 to 5 ethylene glycol units per propylene glycol unit. Examples of nonionic tensides which may be mentioned are: nonylphenolpolyethoxyethanols, castor oil polyglycol ethers, polypropylene/polyethyleneoxy adducts, tributylphenoxypolyethoxyethanol, polyethylene glycol and octylphenoxypolyethoxyethanol. Suitable also are fatty acid esters of polyoxyethylenesorbitan, such as polyoxyethylenesorbitan-trioleate.

In the case of the cationic tensides, they are in particular quaternary ammonium salts which contain as N-substituents at least one alkyl group having 8 to 22 C atoms and, as further substituents, lower, optionally halogenated alkyl, benzyl or lower hydroxyalkyl groups. The salts are preferably in the form of halides, methyl sulfates or ethyl sulfates, for example stearyltrimethylammonium chloride or benzyldi(2-chloroethyl)ethylammonium bromide.

The tensides customarily used in formulation practice are described, inter alia, in the following publication: "Mc Cutcheon's Detergents and Emulsifers Annual", MC Publishing Corp., Ringwood, N.J., 1979.

The pesticidal preparations contain as a rule 0.1 to 99%, particularly 0.1 to 95%, of active substance of the formula I, 1 to 99.9% of a solid or liquid additive, and 0 to 25%, especially 0.1 to 25%, of a tenside. Whereas commercial products are preferably in the form of concentrated compositions, the compositions employed by the end-user are as a rule diluted.

The compositions can also contain additives such as stabilisers, antifoam agents, viscosity regulators, binders and adhesives, as well as fertilisers or other active substances for obtaining special effects.

Formulation examples for liquid active substances of the formula I (%=percent by weight)

| 1. Emulsion concentrates | (a) | (b) | (c) |
|---|---|---|---|
| active substance, | 20% | 40% | 50% |
| calcium dodecylbenzenesulfonate | 5% | 8% | 5.8% |
| castor oil-polyethylene glycol ether (36 mols of ethylene oxide) | 5% | — | — |
| tributylphenol-polyethylene glycol ether (30 mols of ethylene oxide) | — | 12% | 4.2% |
| cyclohexanone | — | 15% | 20% |
| xylene mixture | 70% | 25% | 20% |

Emulsions of any required concentration can be produced from concentrates of this type by dilution with water.

| 2. Solutions | (a) | (b) | (c) | (d) |
|---|---|---|---|---|
| active substance | 80% | 10% | 5% | 95% |
| ethylene glycol-monomethyl ether | 20% | — | — | — |
| polyethylene glycol M G 400 | — | 70% | — | — |
| N—methyl-2-pyrrolidone | — | 20% | — | — |
| epoxidised coconut oil | — | — | 1% | 5% |
| ligroin (boiling limits 160-190° C.) | — | — | 94% | — |

The solutions are suitable for application in the form of the smallest possible drops.

| 3. Granulates | (a) | (b) |
|---|---|---|
| active substance | 5% | 10% |
| kaolin | 94% | — |
| highly dispersed silicic acid | 1% | — |
| attapulgite | — | 90% |

The active substance is dissolved in methylene chloride, the solution is sprayed onto the carrier, and the solvent is subsequently evaporated off in vacuo.

| 4. Dusts | (a) | (b) |
|---|---|---|
| active substance | 2% | 5% |
| highly dispersed silicic acid | 1% | 5% |
| talcum | 97% | — |
| kaolin | — | 90% |

Ready-for-use dusts are obtained by the intimate mixing together of the carriers with the active substance.

Formulation examples for solid active substances of the formula I (%=percent by weight)

| 5. Wettable powders | (a) | (b) |
|---|---|---|
| active substance | 20% | 60% |
| sodium lignin sulfonate | 5% | 5% |
| sodium lauryl sulfate | 3% | — |
| sodium diisobutylnaphthalene sulfonate | — | 6% |
| octylphenolpolyethylene glycol ether (7-8 mols of ethylene oxide) | — | 2% |
| highly dispersed silicic acid | 5% | 27% |
| kaolin | 67% | — |

The active substance is well mixed with the additives and the mixture is thoroughly ground is a suitable mill. Wettable powders which can be diluted with water to give suspensions of the required concentration are obtained.

| 6. Emulsion concentrate | |
|---|---|
| active substance | 10% |
| octylphenol polyethylene glycol ether (4-5 mols of ethylene oxide) | 3% |
| calcium dodecylbenzenesulfonate | 3% |
| castor oil polyglycol ether (36 mols of ethylene oxide) | 4% |
| cyclohexanone | 30% |
| xylene mixture | 50% |

Emulsions of the required concentration can be obtained from this concentrate by dilution with water.

| 7. Dusts | (a) | (b) |
|---|---|---|
| active substance | 5% | 8% |
| talcum | 95% | — |
| kaolin | — | 92% |

Dusts ready for use are obtained by mixing the active substance with the carrier and grinding the mixture in a suitable mill.

| 8. Extruder granulate | |
|---|---|
| active substance | 10% |
| sodium lignin sulfonate | 2% |
| carboxymethylcellulose | 1% |
| kaolin | 87% |

The active substance is mixed and ground with the additives, and the mixture is moistened with water. This mixture is extruded and then dried in a stream of air.

| 9. Coated granulate | |
|---|---|
| active substance | 3% |
| polyethylene glycol (M G 200) | 3% |
| kaolin | 94% |

The finely ground active substance is evenly applied, in a mixer, to the kaolin moistened with polyethylene glycol. Dustfree coated granulates are obtained in this manner.

| 10. Suspension concentrate | |
|---|---|
| active substance | 40% |
| ethylene glycol | 10% |
| nonylphenolpolyethylene glycol ether (15 mols of ethylene oxide) | 6% |
| sodium lignin sulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active substance is intimately mixed with the additives. There is thus obtained a suspension concentrate from which can be produced, by dilution with water, suspensions of the concentration required.

EXAMPLE 1

(a) Production of the compound of the formula

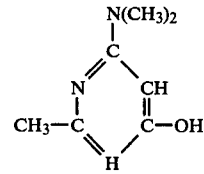

54.3 g of 2-methyl-4-chloro-6-hydroxypyrimidine hydrochloride and 100 ml of alcoholic dimethylamine solution (33%) are heated for 10 hours at 100° C. After cooling, the finely granular suspension is filtered, and the residue is stirred up in 800 ml of water, and the pH value is adjusted to 10–11 with concentrated sodium hydroxide solution. The heated suspension is filtered, and the filtrate is brought to pH 6 with acetic acid. After cooling, the crystals which have precipitated are filtered off, and then recrystallised from methyl alcohol, m.p. 223°–225° C.

(b) Production of the compound of the formula

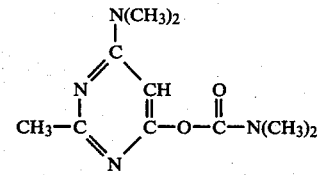

4 g of 2-methyl-4-dimethylamino-6-hydroxy-pyrimidine, 2.8 g of dimethylcarbamoyl chloride, 2.7 g of triethylamine and 0.2 g of dimethylamino-pyridine in 200 ml of chloroform are refluxed for 20 hours. After the filtering off of the insoluble constituents and removal of the solvent, the crude product is recrystallised in ether/pentane; m.p. 58°–65° C.

The following compounds are produced in an analogous manner:

$$\begin{array}{c}R_1\diagdown\phantom{N}\diagup R_2\\N\\|\\C\\\diagup\diagdown\\N\phantom{CCCC}CH\\CH_3-C\phantom{CC}C-OCON(CH_3)_2\\\diagdown\diagup\\N\end{array}$$

| $R_1$ | $R_2$ | Physical data |
|---|---|---|
| $\begin{array}{c}CH_3\\|\\CH_3-C-\\|\\CH_3\end{array}$ | H | m.p.: 111–113° C. |
| $CH_3-$ | H | m.p.: 73–75° C. |
| $CH_2=CH-CH_2-$ | H | m.p.: 68–69° C. |
| $C_2H_5-$ | H | m.p.: 95–97° C. |
| $C_2H_5-$ | $C_2H_5-$ | m.p.: 92–93° C. |
| $CH_3-CH_2-CH_2-$ | H | m.p.: 86–88° C. |
| $\begin{array}{c}CH_3\diagdown\\\phantom{CH}CH-\\CH_3\diagup\end{array}$ | H | $n_D^{20°} = 1,5261$ |
| $\begin{array}{c}CH_2\diagdown\\|\phantom{C}CH-\\CH_2\diagup\end{array}$ | H | m.p. 118–120° C. |
| $CH_2=CH-CH_2-$ | $CH_2=CH-CH_2-$ | $n_D^{20°} = 1,5390$ |
| $CH\equiv C-CH_2-$ | H | m.p.: 118–120° C. |
| $-CH_2-CH_2-CH_2-CH_2-$ | | m.p.: 101–102° C. |
| H | H | m.p.: 156–57° C. |

EXAMPLE 2

Insecticidal contact action: *Aphis craccivora* and *Myzus persicae*

Plants (*Vicia faba*) grown in pots are each infested, before commencement of the test, with about 200 individuals of the species *Aphis fabae* and *Myzus persicae*, respectively. The plants treated in this manner are sprayed dripping wet, 24 hours later, with a solution containing 200 and 100 ppm, respectively, of the compound to be tested. Two plants are used per test compound and per concentration, and an assessment of the mortality rate achieved is made after a further 24 hours.

The compounds according to Example 1 exhibit in the above test, against insects of the species Aphis craccivora and Myzus persicae, the level of activity shown in the following Table.

EXAMPLE 3

Insecticidal action (systemic): *Aphis craccivora*

Rooted bean plants are transplanted into pots each containing 600 ccm of soil; and 50 ml of a solution of the compound to be tested (obtained from a 25% wettable powder), at a concentration of 50 ppm and 10 ppm, respectively, are poured directly onto the soil. After 24 hours, aphids of the species Aphis craccivora are settled onto the parts of plants above the soil, and a plastics cylinder is placed over each plant and drawn to by tying at the bottom in order to protect the aphids from any contact or gas action of the test substance. The evaluation of the mortality rate achieved is made 48 and 72 hours after commencement of the test. Two plants, each in a separate pot, are used per concentration level of test substance. The test is carried out at 25° C. with 70% relative humidity.

In the above test, the compounds according to Example 1 exhibit against insects of the specied *Aphis craccivora*, the systemic action shown in the following Table.

Biological test results

The following Table shows the test results based on the Examples given in the foregoing, the index of values with regard to the percentage mortality of the pests being as follows:

A: 70–100% mortality with 10 ppm of active substance,
B: 70–100% mortality with 50 ppm of active substance,
C: 70–100% mortality with 100 ppm of active substance, and
D: 70–100% mortality with 200 ppm of active substance.

Compounds $$\begin{array}{c}R_1\diagdown\phantom{N}\diagup R_2\\N\\|\\C\\\diagup\diagdown\\N\phantom{CCCC}CH\\CH_3-C\phantom{CC}C-OCON(CH_3)_2\\\diagdown\diagup\\N\end{array}$$

| $R_1$ | $R_2$ | Contact action against *Aphis craccivora* | Systemic action against *Aphis craccivora* |
|---|---|---|---|
| $CH_3-$ | $CH_3-$ | C | A |
| $\begin{array}{c}CH_3\\|\\CH_3-C-\\|\\CH_3\end{array}$ | H | D | B |
| $CH_3-$ | H | C | A |
| $CH_2=CH-CH_2-$ | H | C | A |
| $C_2H_5-$ | $C_2H_5-$ | C | A |
| $\begin{array}{c}CH_3\diagdown\\\phantom{CH}CH-\\CH_3\diagup\end{array}$ | H | C | A |
| $CH_2=CH-CH_2-$ | $CH_2=CH-CH_2-$ | D | B |
| $CH\equiv C-CH_2-$ | H | C | A |
| $-CH_2-CH_2-CH_2-CH_2-$ | | D | B |

What is claimed is:

1. A compound of the formula:

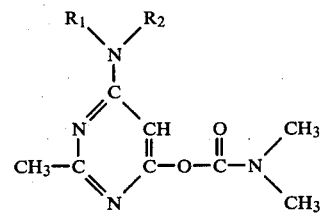

wherein each of $R_1$ and $R_2$, when taken independently, is hydrogen, alkyl of 1 to 5 carbon atoms, cycloalkyl of 3 to 6 carbon atoms, alkenyl of 2 to 5 carbon atoms, or alkynyl of 2 to 5 carbon atoms, or $R_1$ and $R_2$ taken together are alkylene of 2 to 5 carbon atoms.

2. A compound according to claim 11 wherein each of $R_1$ and $R_2$, when taken independently, is hydrogen, alkyl of 1 to 4 carbon atoms, cyclopropyl, allyl or propargyl, or $R_1$ and $R_2$ taken together are tetramethylene.

3. The compound according to claim 2 of the formula

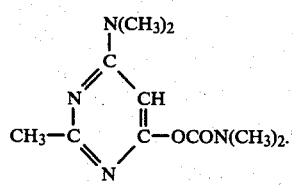

4. The compound according to claim 2 of the formula

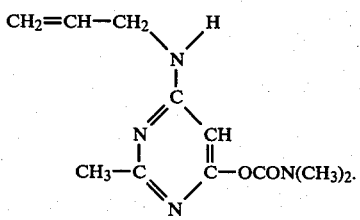

5. The compound according to claim 2 of the formula

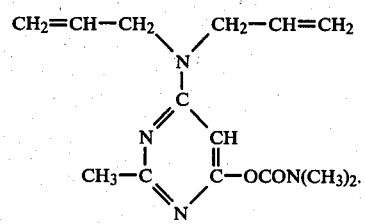

6. The compound according to claim 2 of the formula

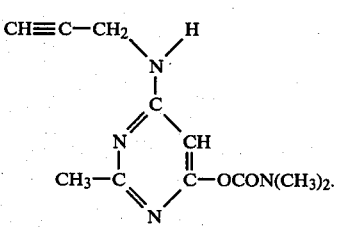

7. The compound according to claim 2 of the formula

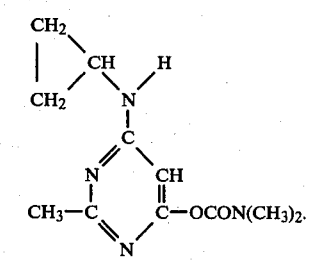

8. A pesticidal composition which contains as active ingredient a compound according to claim 1, together with suitable carriers and/or other additives.

9. A method of combating pests on animals and plants, which method comprises applying thereto or to the locus thereof an effective amount of a compound according to claim 1.

* * * * *